United States Patent [19]

Schäefer et al.

[11] Patent Number: 4,789,561

[45] Date of Patent: Dec. 6, 1988

[54] OXYGEN ELECTRODE WITH LAYER COMPRISING ELECTRODE AND ELECTROLYTE MATERIALS

[75] Inventors: Wolfgang Schäefer, Friedrichshafen; Rainer Schmidberger, Markdorf, both of Fed. Rep. of Germany

[73] Assignee: Dornier System GmbH, Friedrichshafen, Fed. Rep. of Germany

[21] Appl. No.: 33,172

[22] Filed: Apr. 1, 1987

[30] Foreign Application Priority Data

Apr. 4, 1986 [DE] Fed. Rep. of Germany ....... 3611291

[51] Int. Cl.$^4$ .................... B05D 5/12; G01N 27/26; H01M 8/10; H01M 4/58
[52] U.S. Cl. .................... 427/126.1; 427/419.3; 204/421; 204/424; 204/426; 429/33; 429/41; 429/193; 429/218; 429/248
[58] Field of Search ............... 429/30, 31, 32, 33, 429/41, 193, 218, 248; 427/115, 126.2, 419.3; 204/421, 424, 426

[56] References Cited

U.S. PATENT DOCUMENTS 4,481,237 11/1984 Bosshart et al. ............... 427/419.3
4,547,437 10/1985 Isenberg et al. ............... 429/30
4,562,124 12/1985 Ruka .................... 429/30

Primary Examiner—Norman Morgenstern
Assistant Examiner—M. Burke
Attorney, Agent, or Firm—Ralf H. Siegemund

[57] ABSTRACT

The electrode is made by depositing a slurry as a first layer onto a solid electrolyte ceramic of stabilized $ZrO_2$. The slurry is a blend of a powder of a ceramic electronic conductor such as $La_{1-x}Ca_xMn_{1+y}O_3$ or $La_{1-x}SR_xSr_zMn_{1+y}O_3$ and a powder of a ceramic ionic conductor being of the same kind as the electrolyte. Onto the first layer a slurry of powder of the same ceramic electronic conductor used in the first slurry is deposited as a second layer. The layers are deposited by coating or dipping and are fired simultaneously thereafter or sequentially following respective application.

8 Claims, 1 Drawing Sheet

CONSTRUCTION OF AN ELEKTRODE-ELECTROLYTE-INTERFACE AS PER THE INVENTION

CONSTRUCTION OF AN ELEKTROLYSISELL WITH SOLID TELEKTROLYTE

CONSTRUCTION OF AN ELEKTRODE-ELECTROLYTE-INTERFACE AS PER THE INVENTION

OXYGEN ELECTRODE WITH LAYER COMPRISING ELECTRODE AND ELECTROLYTE MATERIALS

BACKGROUND OF THE INVENTION

The present invention relates to an oxygen electrode for use in electrolytic cells under utilization of a solid electrolyte, the electrode is to have a long duration of use. In particular, the invention relates to such an electrode, being a chemically highly effective oxygen electrode, and wherein a solid electrolyte is used to be physically combined with a ceramic compound material upon which the electrode is deposited.

The known oxygen containing electrodes are useful at the present time for a short duration of use only, and, therefore, can be used only in an environment in which the short use life is tolerable. As soon as a longer duration of use is required, the emerging oxygen will separate electrode particles from the interface. This separation reduces the effective contact area between electrolyte and electrode, and, therefore, changes the resulting overall contact resistance so that the electrical loss voltage increases. Therefore, there is a need for a new concept concerning specifically the interface between an electrode and the electrolyte, particularly in the case of an oxygen containing electrode and of a solid electrolyte. The loss voltage has been reduced and the electrical chemical effectiveness of such electrodes has been increased by increasing the three phase boundary between electrode, electrolyte and gas. This is obtained for example, by roughening of the contacting surfaces or by using a compound material that is comprised of an ionic conductive material, and an electronic conductive material. These compound materials are then used as an intermediate layer between two materials for examples, for matching different thermal expansion. Here then the compound material is a mixture of the two materials to be connected. The mixture of a powder blend, generally, can be obtain through mixing powder of the components and using a slurry for and depositing the material, e.g. by way of dipping or spraying. German printed patent application No. 2,852,647, for example, also proposes that an unfired layer may be deposited upon another, yet unfired layer, and both layers are fired together.

DESCRIPTION OF THE INVENTION

It is an object of the present invention to provide a new and improved, long lasting, chemically highly effective oxygen electrode whose operating and use life is far greater than that of known oxygen electrodes, and wherein the blockage of a charge transfer is reduced under utilization of increasing the three phase boundary between electrolyte, and electrode and gas.

In accordance with the preferred embodiment of the present invention, it suggested to provide a ceramic, electronic conductive material in the form of a powder; to separately provide a ceramic ionic conductive material, also as a powder and being of the same kind as the electrolyte; to mix or blend these two powders in a slurry so that it can be sprayed onto a solid electrolyte, following which a ceramic electronic conductor is provided, being of the same material as the ceramic electronically conductive ceramic in the blend, but now, as a slurry by it is sprayed onto the previously applied blend; both slurries are fired. The two layers are either fired together after both have been applied, or sequentially, whenever one has been applied which, of course, means a refiring of the earlier layer. One or both of the slurry may be deposited through dipping.

The particular material involved is preferably the following: The electronic conductor used as a component in the intermediate layer blend and by itself as oxygen electrode is preferably comprised of a mixed oxide such as $La_{1-x}Ca_xMn_{1+y}O_3$ or $La_{1-x}Sr_xMn_{1+y}O_3$ with x between 0.2 and 0.6 and y not larger than 0.1. The ceramic ionic conductor should be selected from a group consisting of $CeO_2$, MgO stabilized $ZrO_2$, CaO stabilized $ZrO_2$, $Y_2O_3$ stabilized $ZrO_2$, $Yb_2O_3$ stabilized $ZrO_2$; $ZrO_2$ stabilized with any other rare earth oxide, or one could use a $CeO_2$, $ZrO_2$ blend in any ratio.

DESCRIPTION OF THE DRAWINGS

While the specification concludes with claimed matter which is regarded as the invention, it is believed that the invention, the objects and features of the invention and further objects, features and advantages thereof will be better understood from the following description taken in connection with the accompanying drawings in which:

DETAILED DESCRIPTION OF THE DRAWINGS

Figure 1:
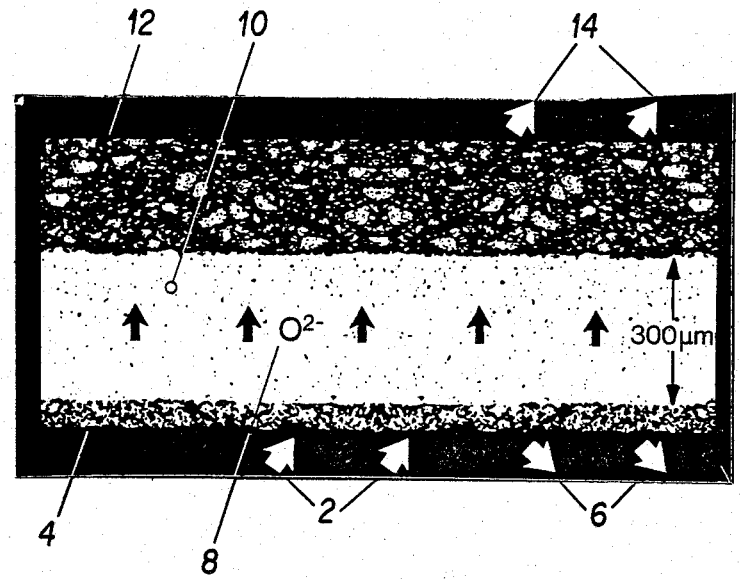
FIG. 1 is a cross-section of an enlarged scale of a micro photographic nature showing an electrolysis cell with a solid electrolyte generally.
Figure 2:
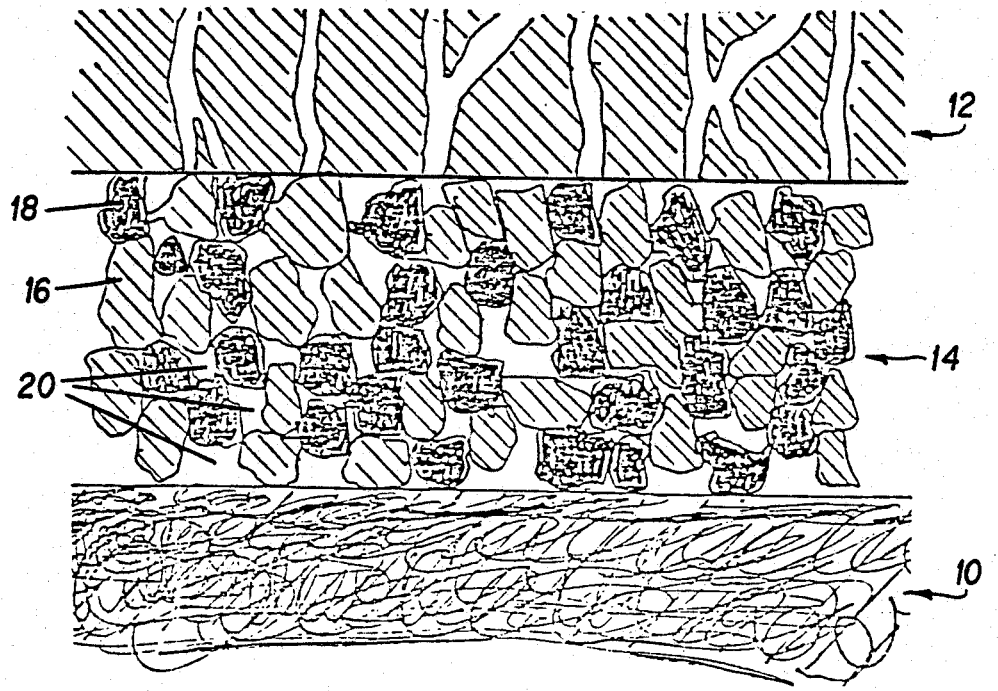
FIG. 2 is a somewhat schematic view of a electrode construction corresponding to the preferred embodiment invention and in an enlarged scale.

FIG. 1 illustrates the construction of an electrolysis cell in accordance with the state of the art, but permitting incorporation of the invention as detailed in FIG. 2. Water vapor (arrows 2) contacts a negatively charged cathode 4. Upon feeding an electric current thereto, the water vapor 2 is separated into hydrogen 6 (downward pointing arrows) and oxygen 8 (black arrows). The hydrogen 6 is removed by the flow 2 of steam itself and as $H_2$, while the oxygen 8 is ionized as $O^{2-}$ and passes through the solid electrolyte 10. The arrows identify the actual (average) direction of movement of the oxygen ions. A solid electrolyte 10 is comprised of $Y_2O_3$ stabilized $ZrO_2$. The anode 12 is positively charged, and the oxygen ions are electrically discharged (neutralized) and emerge as gas $O_2$, being identified by arrows 14. Of particular interest now is the interface between electrolyte 10 and electrode 12.

Turning now to FIG. 2, the interface position in an electrolysis cell is shown, including particularly a transition zone from the solid electrolyte 10 to the positively charged anode 12. This anode 12 constitutes the oxygen electrode within the inventive arrangement, and is illustrated somewhat schematically only. In accordance with the specific feature of the invention, interface 15 between the electrolyte 10 and the anode 12, is established by an intermediate layer. This intermediate layer 15 is made of two components. The two components of the interface material 15, as interposed between the electrolyte 10 and the electrode material 12, are made of ceramics. The two ceramic components are represented by particles 16 and 18, being respectively comprised of the electrode material used for making anode 12 as well as of the electrolyte material 10. Hence, powder particles 16 are of an electronic conducting material and particles 18 are of an ionic conducting material.

A large number of pores 20 exist within the compound material 15. Accordingly, there is realized a large plurality of microscopically small contact areas between the ionically conductive material, on one hand, and the electronic conductive material, on the other hand. The porosity is particularly such that the sum of the effective surface areas of contact is larger than the macroscopic geometric surface of the electrolyte surface as such. Thus, the oxygen development is, in fact, distributed over a large three phase boundary so that large local current densities will not obtain in any microscopic or incremental area. Hence, the charge transfer between ionic conductor and electronic conductor is blocked to a lesser extent. Consequently, ablation of electrode parts through oxygen pressure no longer occurs which, in turn, means that there is a considerable extension in the use life of such an oxygen electrode.

Without changing the composition of the material, one can use an oxygen electrode of the type described also in high temperature fuel cells or in oxygen boundary current probes using a $ZrO_2$ electrolyte.

In the following a specific example is explained by means of which the invention can be practiced with advantage. The solid electrolyte 10 is realized by $Y_2O_3$ stabilized $ZrO_2$. An intermediate layer is sprayed onto this electrolyte as a slurry. This slurry includes a powder blend being comprised of the mixed oxide $La_{1-x}Ca_xMn_{1+y}O_3$, and of $Y_2O_3$ stabilized $ZrO_2$. Values with advantage for this composition are, for example, $x=0.5$ and $y=0.03$. Upon this particular layer, serving now as an intermediate layer, one will spray on the electrode material having exactly the same composition as the mixed oxide but now without the $ZrO_2$. This layer is also sprayed on as a slurry and then both layers are fired at 1250° C.

The invention is not limited to the embodiments described above, but all changes and modifications thereof, not constituting departures from the spirit and scope of the invention are intended to be included.

We claim:

1. Method of making oxygen electrodes for use in electrolysis cell in conjunction with a solid electrolyte and having a long use life, comprising the steps of:
   providing a powder of a ceramic electronic conductor;
   providing a powder of a ceramic ionic conductor being of the same kind as the electrolyte;
   blending said powders in a first slurry;
   forming a first layer by spray coating or dipping a solid electrolyte with or in said first slurry to obtain the first layer on the solid electrolyte;
   providing a second slurry of said ceramic electronic conductor powder;
   providing on said spray coated or dipped, first slurry layer, the second slurry of powder to obtain a second layer also by spray coating or diffusing; and
   firing the first and second layers.

2. Method as in claim 1 wherein said first and second layers are fired simultaneously.

3. Method as in claim 1 wherein the first layer is fired prior to the providing of the second layer.

4. Method as in claim 1, using as the ceramic, electronic conductor a composition of $La_{1-x}Ca_xMn_{1+y}O_3$ or $La_{1-x}Sr_xMn_{1+y}O_3$ with $x=$ to or larger than 0.2 but not larger than 0.6, and $y=$ to or below 0.1.

5. Method as in claim 1, comprising the additional step of using as a ceramic, ionic conductor one of the following $CeO_2$, MgO stabilized $ZrO_2$, CaO stabilized $ZrO_2$, $Y_2O_3$ stabilized $ZrO_2$, $Yb_2O_3$ stabilized $ZrO_2$, other rare earth stabilized $ZrO_2$ or a blend of $CeO_2$ and $ZrO_2$.

6. Method as in claim 1, comprising the step of using the same kind of ceramic material for the electronic conductor as blended and as electrolyte.

7. Method as in claim 6, using as the ceramic, electronic conductor a composition of $La_{1-x}Ca_xMn_{1+y}O_3$ or $La_{1-x}Sr_xMn_{1+y}O_3$ with $x=$ to or larger than 0.2 but not larger than 0.6, and $y=$ to or below 0.1.

8. Method as in claim 6, comprising the additional step of using as a ceramic, ionic conductor one of the following $CeO_2$, MgO stabilized $ZrO_2$, CaO stabilized $ZrO_2$, $Y_2O_3$ stabilized $ZrO_2$, $Yb_2O_3$ stabilized $ZrO_2$, other rare earth stabilized $ZrO_2$ or a blend of $CeO_2$ and $ZrO_2$.

* * * * *